(12) United States Patent
Kim et al.

(10) Patent No.: US 12,324,909 B2
(45) Date of Patent: Jun. 10, 2025

(54) NEURAL ELECTRODE BASED ON THREE-DIMENSIONAL STRUCTURE OF FLEXIBLE SUBSTRATE, AND MANUFACTURING METHOD THEREFOR

(71) Applicant: DAEGU GYEONGBUK INSTITUTE OF SCIENCE AND TECHNOLOGY, Daegu (KR)

(72) Inventors: Sohee Kim, Daegu (KR); Yoona Kang, Daegu (KR); Namju Kim, Daegu (KR)

(73) Assignee: DAEGU GYEONGBUK INSTITUTE OF SCIENCE AND TECHNOLOGY, Daegu (KR)

(*) Notice: Subject to any disclaimer, the term of this patent is extended or adjusted under 35 U.S.C. 154(b) by 416 days.

(21) Appl. No.: 17/611,273

(22) PCT Filed: Nov. 2, 2020

(86) PCT No.: PCT/KR2020/015172
§ 371 (c)(1),
(2) Date: Nov. 15, 2021

(87) PCT Pub. No.: WO2021/101125
PCT Pub. Date: May 27, 2021

(65) Prior Publication Data
US 2022/0339431 A1 Oct. 27, 2022

(30) Foreign Application Priority Data
Nov. 18, 2019 (KR) .................. 10-2019-0148128

(51) Int. Cl.
*A61N 1/04* (2006.01)
*A61B 5/24* (2021.01)
(Continued)

(52) U.S. Cl.
CPC .............. *A61N 1/0496* (2013.01); *A61B 5/24* (2021.01); *A61B 5/257* (2021.01); *A61N 1/0529* (2013.01);
(Continued)

(58) Field of Classification Search
CPC .......... A61N 1/0496; A61N 1/05; A61B 5/24; A61B 5/257; A61B 2018/00136; A61B 2562/125
See application file for complete search history.

(56) References Cited

U.S. PATENT DOCUMENTS 6,236,302 B1  5/2001  Barrett et al.
2017/0164853 A1  6/2017  Kim et al.
(Continued)

FOREIGN PATENT DOCUMENTS

JP  2018023494  2/2018
KR  20010087389  9/2001
(Continued)

OTHER PUBLICATIONS

KIPO, Office Action of KR 10-2019-0148128 dated Aug. 31, 2021.
KIPO, PCT Search Report & Written Opinion of PCT/KR2020/015172 dated Jun. 8, 2021.

*Primary Examiner* — Linda C Dvorak
*Assistant Examiner* — Abigail Bock
(74) *Attorney, Agent, or Firm* — LEX IP MEISTER, PLLC (57) ABSTRACT

One embodiment of the present invention provides a flexible neural electrode having improved adherence to an object by using a three-dimensional structure. A neural electrode based on the three-dimensional structure of a flexible substrate, according to one embodiment of the present invention, comprises: a first polymer layer, which is formed from a polymer material, is flexible, and functions as a base; at least one photoresist part, which is formed on one portion of
(Continued)

the surface of the first polymer layer and forms a three-dimensional structure; a second polymer layer which is formed on the photoresist part and the rest of the surface of the first polymer layer, and which comprises protrusion parts caused by the photoresist part; a metal thin film layer formed by patterning a metal thin film on the surface of the second polymer layer and the surface of the protrusion parts; and a third polymer layer which is formed on the surface of the second polymer layer and the metal thin film layer so as to function as a covering, and which comprises measurement holes formed so that one portion of the metal thin film layer formed at the ends of the protrusion parts is exposed to the outside.

4 Claims, 6 Drawing Sheets

(51) Int. Cl.
 *A61B 5/257* (2021.01)
 *A61B 18/00* (2006.01)
 *A61N 1/05* (2006.01)

(52) U.S. Cl.
 CPC ............... *A61B 2018/00136* (2013.01); *A61B 2562/125* (2013.01)

(56) References Cited

U.S. PATENT DOCUMENTS

| | | |
|---|---|---|
| 2019/0254603 A1 | 8/2019 | Lang |
| 2019/0308019 A1 | 10/2019 | Kim et al. |

FOREIGN PATENT DOCUMENTS

| | | |
|---|---|---|
| KR | 101033907 | 5/2011 |
| KR | 101452908 | 10/2014 |
| KR | 20170071261 | 6/2017 |
| KR | 20190066062 | 6/2019 |
| KR | 20190116848 | 10/2019 |
| WO | 2014/071153 | 5/2014 |

NEURAL ELECTRODE BASED ON THREE-DIMENSIONAL STRUCTURE OF FLEXIBLE SUBSTRATE, AND MANUFACTURING METHOD THEREFOR

TECHNICAL FIELD

The disclosure relates to a neural electrode having improved selective adhesion to a target portion by using a three-dimensional structure of a flexible substrate, and a manufacturing method therefor, and more particularly, to a flexible neural electrode having improved adhesion to an object by using a three-dimensional structure.

BACKGROUND ART

A planar neural electrode that measures or stimulates a neural signal from a nerve cell of a brain or a peripheral nerve may be placed on a surface of the brain or may surround the peripheral nerve. Such a planar electrode may be used for a surface having many curves or a complex shape, and its adhesion may thus be an important issue in the related art. Accordingly, in order to increase adhesion between the planar electrode and an object, there has been a continuous research and development to enable the electrode to have a substrate as thin as a thin film or to use a substrate made of a flexible polymer material.

However, in case of using the prior art, the flexible planar electrode is limited to have a two-dimensional structure formed by the vapor deposition and patterning processes of the polymer substrate and metal, and there may thus be a limit to adhere the two-dimensional electrode fully and closely to the curved object having a three-dimensional structure.

Korean Patent Publication No. 10-1452908 (entitled, "Method and device for manufacturing 3-dimensional protruding neural electrode") discloses a three-dimensional neural electrode including a lower plate placed at a lower portion of a planar neural electrode, an upper plate placed at an upper portion of the planar neural electrode, and a thermal pressure part connected to the lower plate and the upper plate and applying heat or pressure to the lower plate and the upper plate, in which one of the lower plate and the upper plate includes a convex part having an embossed shape and the other includes a concave part having an engraving shape.

DISCLOSURE

Technical Problem

The disclosure provides a flexible planar neural electrode having improved selective adhesion to an object.

The disclosure also provides a neural electrode having a three-dimensional structure, in which this three-dimensional structure may be formed by a simple process.

Technical tasks of the disclosure are not limited to those mentioned above, and other tasks not mentioned here may be obviously understood by those skilled in the art to which the disclosure pertains from the following description.

Technical Solution

According to an embodiment of the disclosure, a neural electrode based on a three-dimensional structure of a flexible substrate includes: a flexible first polymer layer made of a polymer material and functioning as a base; at least one photoresist part formed on one portion of a surface of the first polymer layer and forming a three-dimensional structure; a second polymer layer formed on the rest of the surface of the first polymer layer and the photoresist part, and including a protrusion part formed by the photoresist part; a metal thin film layer formed by patterning a metal thin film on a surface of the second polymer layer and a surface of the protrusion part; and a third polymer layer formed on the surface of the second polymer layer and the metal thin film layer to function as a covering, and including a measurement hole punched for one portion of the metal thin film layer formed at an end of the protrusion part to be exposed to the outside.

According to an embodiment of the disclosure, the first polymer layer may be formed on a wafer.

According to an embodiment of the disclosure, one or more layers selected from the first polymer layer, the second polymer layer or the third polymer layer may be formed by vapor deposition.

According to an embodiment of the disclosure, one or more layers selected from the first polymer layer, the second polymer layer or the third polymer layer may be made of parylene.

According to an embodiment of the disclosure, a manufacturing method of the neural electrode based on a three-dimensional structure of a flexible substrate includes: a first step of preparing the wafer, vapor-depositing a sacrificial layer on a surface of the wafer, and then vapor-depositing the first polymer layer on a surface of the sacrificial layer; a second step of forming the three-dimensional structure by patterning and reflowing the photoresist part on one portion of the surface of the first polymer layer; a third step of vapor-depositing the second polymer layer on the rest of the surface of the first polymer layer and the photoresist part; a fourth step of vapor-depositing the metal thin film layer by vapor-depositing and patterning the metal thin film on the surface of the second polymer layer and the surface of the protrusion part; and a fifth step of vapor-depositing the third polymer layer on the surface of the second polymer layer and the metal thin film layer, and etching one portion of the third polymer layer to form the measurement hole.

According to another embodiment of the disclosure, a neural electrode based on a three-dimensional structure of a flexible substrate includes: a flexible first polymer layer made of a polymer material and functioning as a base; at least one photoresist part formed on one portion of a surface of the first polymer layer and forming a three-dimensional structure; a second polymer layer formed on the rest of the surface of the first polymer layer and the photoresist part, and including a protrusion part formed by the photoresist part; a metal thin film layer formed by patterning a metal thin film on one portion of a surface of the second polymer layer and a surface of the protrusion part; a third polymer layer formed on the surface of the second polymer layer and the metal thin film layer to function as a covering, and including a measurement hole punched for one portion of the metal thin film layer formed at an end of the protrusion part to be exposed to the outside; and a conductive part passing through the first polymer layer and the second polymer layer to be in contact with the metal thin film layer, and connected to an external terminal.

According to another embodiment of the disclosure, the first polymer layer may be formed on a wafer.

According to another embodiment of the disclosure, one or more layers selected from the first polymer layer, the second polymer layer or the third polymer layer may be formed by vapor deposition.

According to another embodiment of the disclosure, one or more layers selected from the first polymer layer, the second polymer layer or the third polymer layer may be made of parylene.

According to another embodiment of the disclosure, the conductive part may be made of conductive epoxy.

According to another embodiment of the disclosure, a manufacturing method of the neural electrode based on a three-dimensional structure of a flexible substrate includes: a first step of preparing the wafer, vapor-depositing a sacrificial layer on a surface of the wafer, and then vapor-depositing the first polymer layer on a surface of the sacrificial layer; a second step of forming the three-dimensional structure by patterning and reflowing the photoresist part on one portion of the surface of the first polymer layer; a third step of vapor-depositing the second polymer layer on the rest of the surface of the first polymer layer and the photoresist part; a fourth step of vapor-depositing the metal thin film layer including a punched portion by vapor-depositing and patterning the metal thin film on one portion of the surface of the second polymer layer and the surface of the protrusion part; a fifth step of vapor-depositing the third polymer layer on the surface of the second polymer layer and the metal thin film layer, and etching one portion of the third polymer layer to form the measurement hole; a sixth step of forming a through hole by punching the first polymer layer, the second polymer layer and the third polymer layer, based on the punched portion of the metal thin film layer; and a seventh step of separating and removing the wafer and the sacrificial layer, and forming the conductive part placed along the through hole and in contact with the metal thin film layer.

According to yet another embodiment of the disclosure, a neural electrode based on a three-dimensional structure of a flexible substrate includes: a flexible first polymer layer made of a polymer material, functioning as a base, and including at least one punched connection hole; a first metal thin film layer formed by patterning a metal thin film on the connection hole and one portion of a surface of the first polymer layer, adjacent to the connection hole; a photoresist part formed on a surface of the first metal thin film layer and forming a three-dimensional structure; a second metal thin film layer formed by a metal thin film on the photoresist part and connected to the first metal thin film layer; a second polymer layer formed on the first metal thin film layer, the second metal thin film layer and the rest of the surface of the first polymer layer to function as a covering, and including a measurement hole punched for one portion of the second metal thin film layer placed at an end of the photoresist part to be exposed to the outside; and a conductive part inserted into the connection hole to be in contact with the first metal thin film layer, and connected to an external terminal.

According to yet another embodiment of the disclosure, the first polymer layer may be formed on a wafer.

According to yet another embodiment of the disclosure, the first polymer layer or the second polymer layer may be formed by vapor deposition.

According to yet another embodiment of the disclosure, the first polymer layer or the second polymer layer may be made of parylene.

According to yet another embodiment of the disclosure, the conductive part may be made of conductive epoxy.

According to yet another embodiment of the disclosure, a manufacturing method of the neural electrode based on a three-dimensional structure of a flexible substrate includes: a first step of preparing the wafer, vapor-depositing a sacrificial layer on a surface of the wafer, then patterning and vapor-depositing the first polymer layer on a surface of the sacrificial layer, and forming the connection hole in the first polymer layer; a second step of inserting a temporary insert into the connection hole to fill the same, and then forming the first metal thin film layer by patterning the metal thin film on the connection hole and the one portion of the surface of the first polymer layer, adjacent to the connection hole; a third step of patterning and reflowing the photoresist part by forming a three-dimensional structure of photoresist on the surface of the first metal thin film layer; a fourth step of forming the second metal thin film layer by patterning the metal thin film on the photoresist part, and connecting the first metal thin film layer and the second metal thin film layer to each other; a fifth step of vapor-depositing the second polymer layer on the first metal thin film layer, the second metal thin film layer and the rest of the surface of the first polymer layer, and etching one portion of the second polymer layer to form the measurement hole; a sixth step of separating and removing the wafer and the sacrificial layer; and a seventh step of removing the temporary insert inserted into the connection hole, and forming the conductive part inserted into the connection hole and in contact with the first metal thin film layer.

Advantageous Effects

The electrode may have a three-dimensional shape based on the above configuration, and the neural electrode and the object may thus have improved adhesion therebetween.

Further, the neural electrode may have any of various shapes by allowing the photoresist parts to form the three-dimensional structures each having a different protrusion height.

Furthermore, it is possible to make its manufacturing method simple and its structure easily modified by sequentially stacking the polymer material and the metal together, further performing only the etching process, and omitting a separate insulation process.

It should be understood that the effects of the disclosure are not limited to the above-described effects, and include all effects which may be inferred from the configuration of the disclosure described in the detailed description or claims of the disclosure.

BEST MODE

Hereinafter, embodiments of the disclosure are described with reference to the accompanying drawings. However, the disclosure may be implemented in various different forms and is not limited to the embodiments described herein. In addition, in the drawings, portions unrelated to the description are omitted to clearly describe the disclosure, and similar portions are denoted by similar reference numerals throughout the specification.

Throughout the present specification, in case that any one part is referred to as being "connected (contacted, combined, coupled) to" another part, it means that any one part and another part are "directly connected to" each other or are "indirectly connected to" each other with another member interposed therebetween. In addition, unless explicitly described to the contrary, "including" any component will be understood to imply the inclusion of other components rather than the exclusion of any other components.

Terms used in the present specification are used only in order to describe specific embodiments rather than limiting the disclosure. Singular forms used herein are intended to include plural forms unless explicitly indicated otherwise. It should be further understood that terms "include" or "have" used in the present specification specify the presence of features, numerals, steps, operations, components, parts mentioned in the present specification or combinations thereof, but do not preclude the presence or addition of one or more other features, numerals, steps, operations, components, parts or combinations thereof.

The disclosure relates to a neural electrode that measures or stimulates a neural signal from a nerve cell of a brain or a peripheral nerve, in which the neural electrode may be placed on a surface of an organ including the nerve cell, such as the brain or may surround the peripheral nerve. That is, its target object may be the brain, an eyeball, the peripheral nerve, etc. Hereinafter, the embodiments of the disclosure are described in detail with reference to the accompanying drawings.

First, the description describes a neural electrode according to one embodiment of the disclosure.

Figure 1:
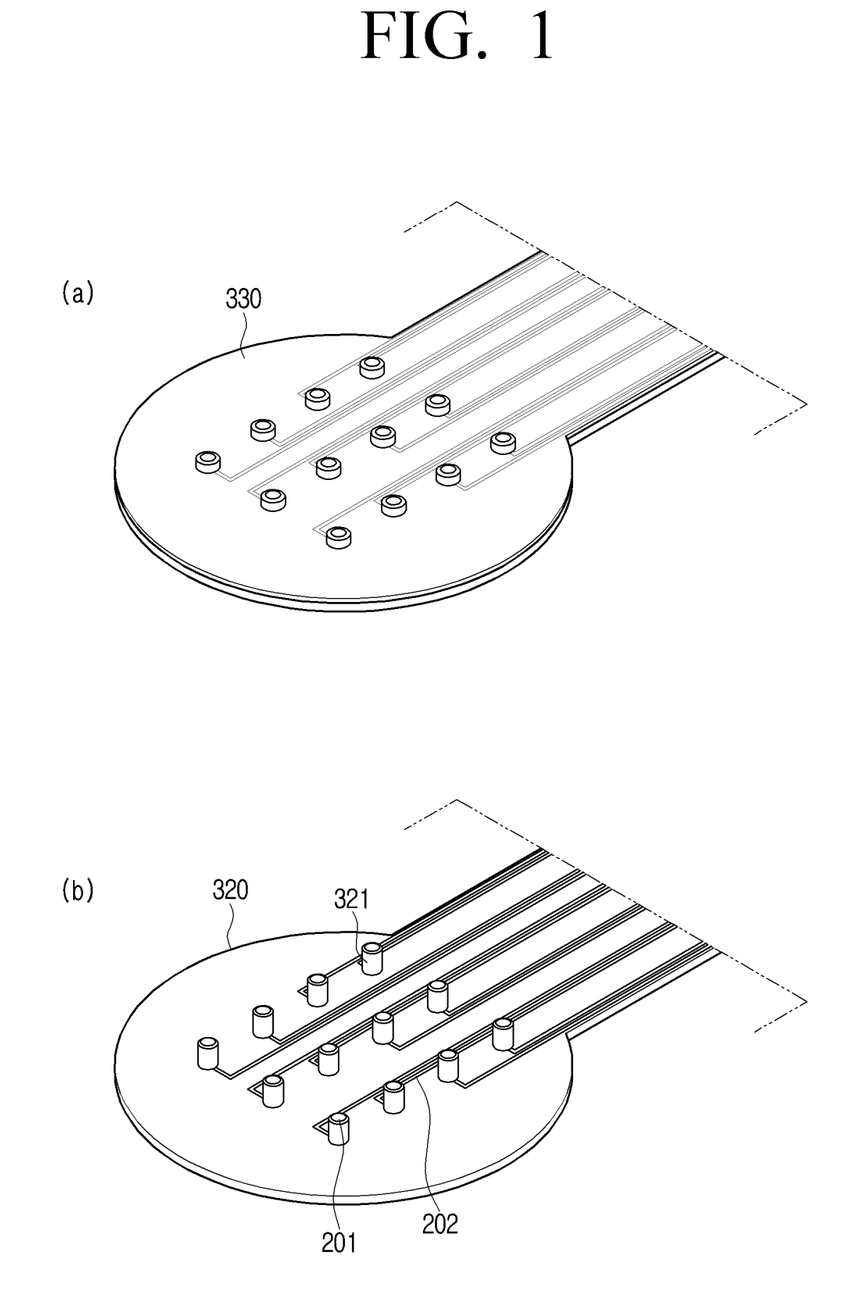
FIG. 1 shows the external perspective view and internal configuration diagram of a neural electrode according to one embodiment of the disclosure.
Figure 2:
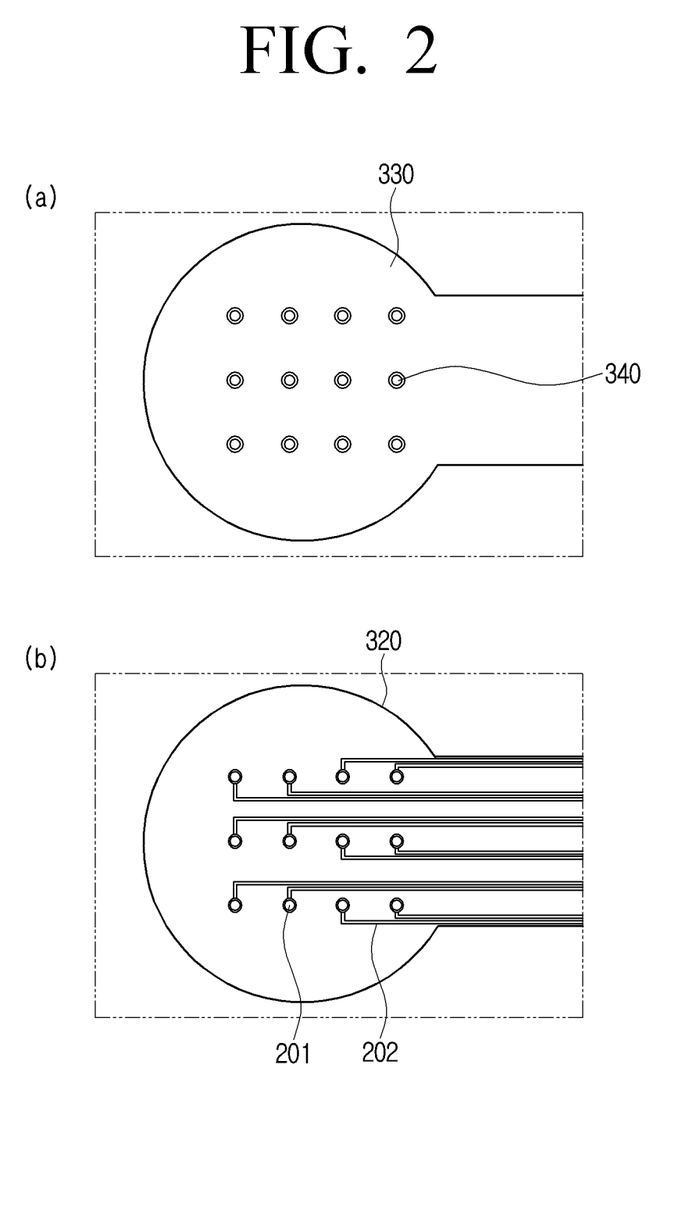
FIG. 2 shows an external plane view of the neural electrode according to one embodiment of the disclosure and a plane view of its internal configuration.
Figure 3:
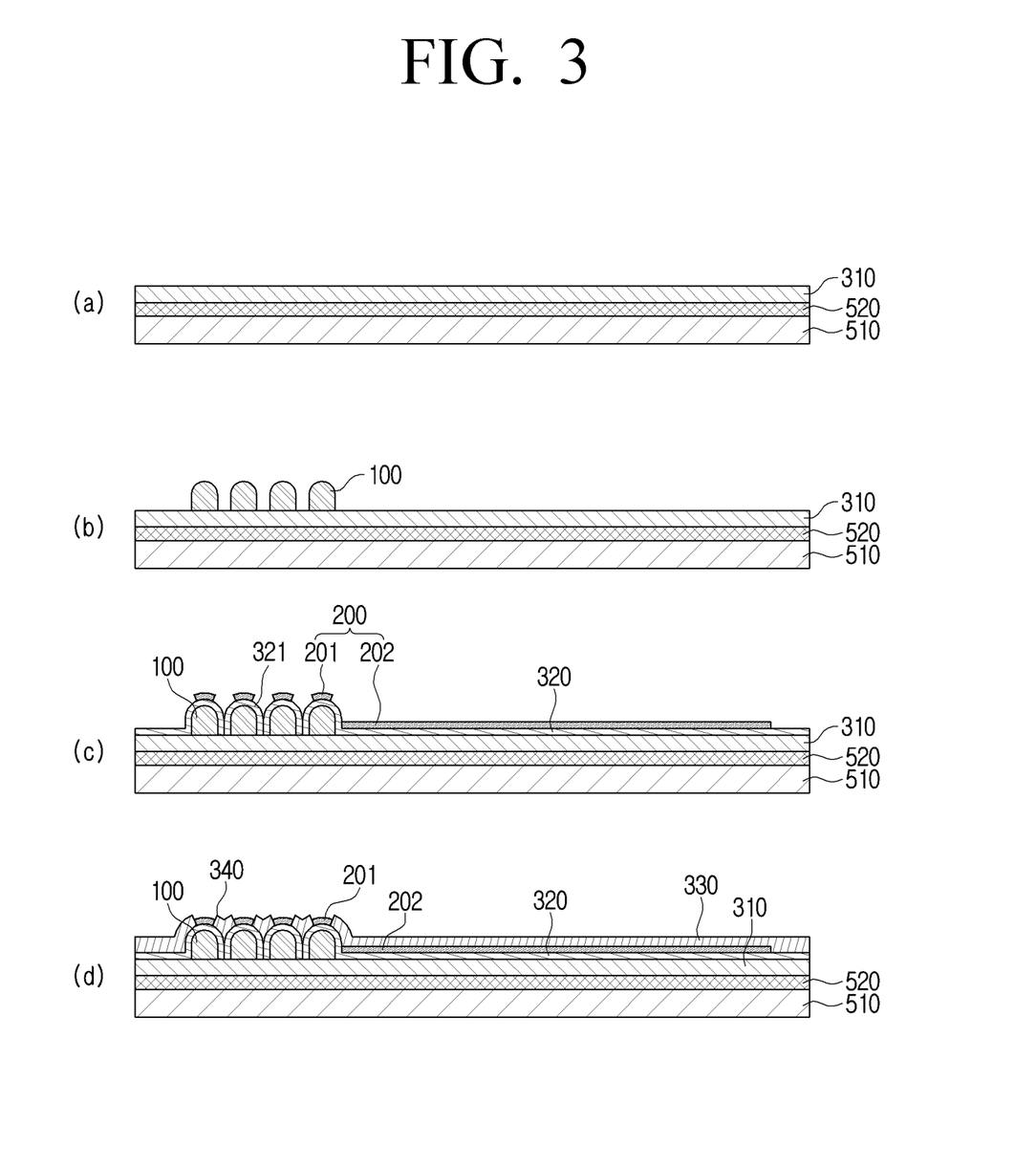
FIG. 3 shows cross-sectional views showing a manufacturing process of the neural electrode according to one embodiment of the disclosure.
Figure 4:
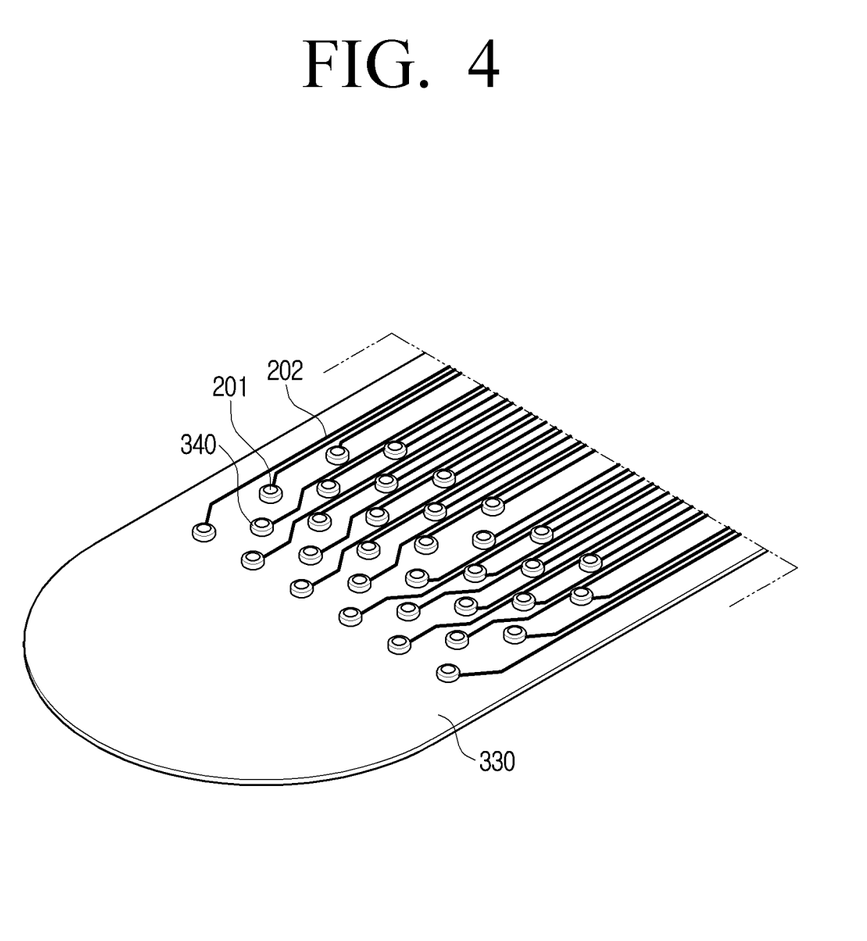
FIG. 4 shows an image of the neural electrode according to one embodiment of the disclosure.

FIG. 1 shows the external perspective view and internal configuration diagram of a neural electrode according to one embodiment of the disclosure, and FIG. 2 shows an external plane view of the neural electrode according to one embodiment of the disclosure and a plane view of its internal configuration. In addition, FIG. 3 shows cross-sectional views showing a manufacturing process of the neural electrode according to one embodiment of the disclosure, and FIG. 4 shows an image of the neural electrode according to one embodiment of the disclosure.

FIG. 1A shows the external perspective view of the neural electrode according to one embodiment of the disclosure; and FIG. 1B shows the internal configuration diagram of the neural electrode according to one embodiment of the disclosure from which a third polymer layer 330 is excluded. In addition, FIG. 2A shows the external plane view of the neural electrode according to one embodiment of the disclosure; and FIG. 2B shows the internal configuration diagram of the neural electrode according to one embodiment of the disclosure from which the third polymer layer 330 is excluded. FIG. 3 is referenced below in the detailed description of a manufacturing method of the neural electrode.

As shown in FIGS. 1 to 4, the neural electrode according to one embodiment of the disclosure includes: a flexible first polymer layer 310 made of a polymer material and functioning as a base; at least one photoresist part 100 formed on one portion of a surface of the first polymer layer 310 and forming a three-dimensional structure; a second polymer layer 320 formed on the rest of the surface of the first polymer layer 310 and the photoresist part 100, and including a protrusion part 321 formed by the photoresist part 100; a metal thin film layer 200 formed by patterning a metal thin film on a surface of the second polymer layer 320 and a surface of the protrusion part 321; and a third polymer layer 330 formed on the surface of the second polymer layer 320 and the metal thin film layer 200 to function as a covering, and including a measurement hole 340 punched for one portion of the metal thin film layer 200 formed at an end of the protrusion part 321 to be exposed to the outside.

One or more layers selected from the first polymer layer 310, the second polymer layer 320 or the third polymer layer 330 may be made of parylene. The parylene is a plastic obtained by polymerization of paraxylene, and is harmless to a human body. In case of performing parylene coating on a predetermined surface using parylene coating equipment of the prior art, the parylene may be vapor-deposited and coated on a surface of an object in a micrometer (μm) thickness unit. The parylene coating equipment belongs to the prior art, and the description thus omits details of using the same.

This embodiment of the disclosure describes that one or more layers selected from the first polymer layer 310, the second polymer layer 320 or the third polymer layer 330 are formed of the parylene. However, the layers are not limited thereto, and may use any material harmless to the human body and capable of forming a coating layer having a thickness of micrometer (μm) or nanometer (nm) unit.

The photoresist part 100 may be made of photoresist which is a polymer material whose resistance to a chemical is changed by being exposed to light. The photoresist part 100 may be formed by patterning the photoresist on the first polymer layer 310 to pattern the three-dimensional structure of the photoresist, and reflowing the three-dimensional structure of the photoresist using a photoresist reflow device. The photoresist reflow device belongs to the prior art, and the description thus omits details of using the same.

One or more layers selected from the first polymer layer 310, the second polymer layer 320 or the third polymer layer 330 may be formed by vapor deposition. In detail, one or more layers selected from the first polymer layer 310, the second polymer layer 320 or the third polymer layer 330 may be formed by chemical vapor deposition. In addition, as described above, in case that each layer is made of the parylene, each layer may be formed by being chemically vapor-deposited using the parylene coating equipment.

The metal thin film layer 200 may be made of one or more materials selected from a group consisting of gold (Au), platinum (Pt), iridium (Ir) and iridium oxide (IrOx). The metal thin film layer 200 may be vapor-deposited on the surface of the second polymer layer 320 and the surface of the protrusion part 321, and may be vapor-deposited by a sputtering process or a chemical vapor deposition (CVD) process.

The metal thin film layer 200 may include a measuring thin film 201 formed at the end of the protrusion part 321 and along a body surface of the protrusion part 321, and a transmission line 202 connected to the measuring thin film 201, formed along the surface of the second polymer layer 320 and connected to an external terminal. One portion of the measuring thin film 201, exposed through the measurement hole 340, may be in contact with an object.

The measuring thin film 201 may be exposed to the outside through the measurement hole 340 and may come into contact with the object. In addition, in case that the plurality of protrusion parts 321 are formed by the plurality of photoresist parts 100, each of the plurality of measuring thin films 201 may be formed on the end and body surface of the protrusion part 321, the plurality of transmission lines 202 each connected to the plurality of measuring thin films 201 are formed and disposed along the surface of the second polymer layer 320, and each transmission line 202 may be connected to the external terminal. An electrical signal may be exchanged between the external terminal and the measuring thin film 201 through the transmission line 202.

The first polymer layer 310 may be formed on a wafer 510. Here, a sacrificial layer 520 may be formed between the first polymer layer 310 and the wafer 510. The sacrificial layer 520 may be formed between the first polymer layer 310 and the wafer 510, and may be selectively removed to perform a function of allowing the wafer 510 to be separated from the first polymer layer 310. The sacrificial layer 520 may use a material such as polyvinyl alcohol (PVA), polymethyl methacrylate (PMMA) or polystyrene (PS), which is selectively dissolved only in an organic solvent such as water, acetone or toluene.

Hereinafter, the description describes a manufacturing method of the neural electrode according to one embodiment of the disclosure. FIG. 3A shows the cross-sectional view in which a wafer 510, a sacrificial layer 520 and the first polymer layer 310 are sequentially stacked together; and FIG. 3B shows the cross-sectional view in which the photoresist part 100 is formed on the surface of the first polymer layer 310. In addition, FIG. 3C shows the cross-sectional view in which the second polymer layer 320 is formed on the surface of the first polymer layer 310 and the photoresist part 100, and the metal thin film layer 200 is then formed on the surface of the second polymer layer 320 and the surface of the protrusion part 321. In addition, FIG. 3D shows the cross-sectional view in which the third polymer layer 330 is formed on the surface of the second polymer layer 320 and the metal thin film layer 200.

First, FIG. 3A shows a first step of preparing the wafer 510, vapor-depositing the sacrificial layer 520 on a surface of the wafer 510, and then vapor-depositing the first polymer layer 310 on a surface of the sacrificial layer 520. Here, an expression that a layer is vapor-deposited may indicate that the layer is formed. The rest is the same.

Next, FIG. 3B shows a second step of forming the three-dimensional structure by patterning and reflowing the photoresist part 100 on one portion of the surface of the first polymer layer 310. In addition, FIG. 3C shows a third step of vapor-depositing the second polymer layer 320 on the rest of the surface of the first polymer layer 310 and the photoresist part 100, and a fourth step of vapor-depositing the metal thin film layer 200 by vapor-depositing and patterning the metal thin film on the surface of the second polymer layer 320 and the surface of the protrusion part 321.

Subsequently, FIG. 3D shows a fifth step of vapor-depositing the third polymer layer 330 on the surface of the second polymer layer 320 and the metal thin film layer 200, and etching one portion of the third polymer layer 330 to form the measurement hole 340. As described above, the measurement hole 340 may be formed by etching the one portion of the third polymer layer 330 and punching the same. The one portion of the third polymer layer 330 may be etched by using dry etching capable of fine patterning. However, the etching method is not limited thereto, and wet etching may be used. Finally, after the fifth step, the sacrificial layer 520 may be removed to separate the wafer 510 from the first polymer layer 310. Here, the sacrificial layer 520 may be removed by being dissolved in the organic solvent.

Figure 5:
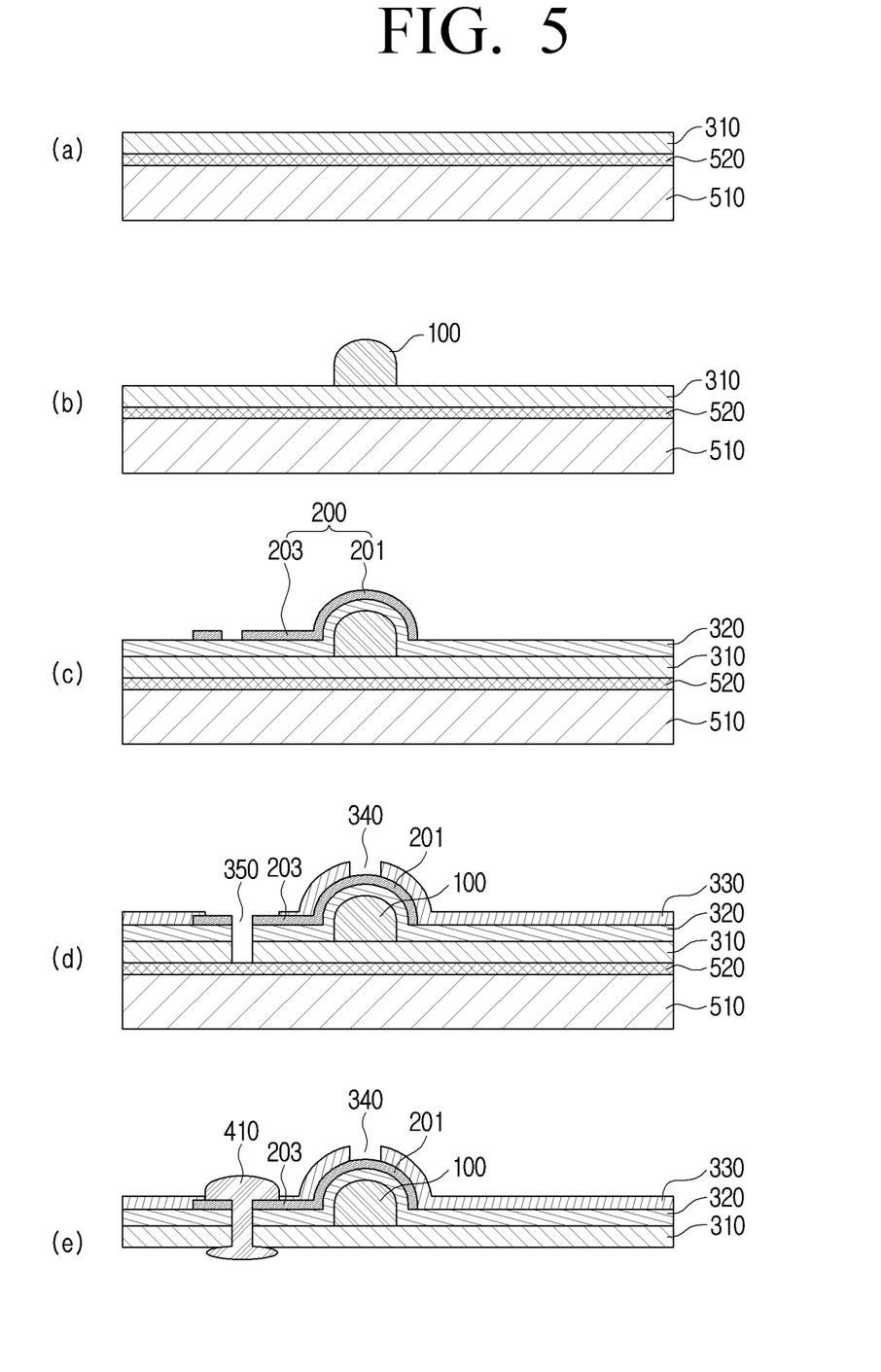
FIG. 5 shows cross-sectional views showing a manufacturing process of a neural electrode according to another embodiment of the disclosure.

Hereinafter, the description describes a neural electrode according to another embodiment of the disclosure. FIG. 5 shows cross-sectional views showing a manufacturing process of a neural electrode according to another embodiment of the disclosure. Here, FIG. 5A shows the cross-sectional view in which a wafer 510, a sacrificial layer 520 and a first polymer layer 310 are sequentially stacked together; and FIG. 5B shows the cross-sectional view in which a photoresist part 100 is formed on a surface of the first polymer layer 310. In addition, FIG. 5C shows the cross-sectional view in which a second polymer layer 320 is formed on the surface of the first polymer layer 310 and the photoresist part 100, and a metal thin film layer 200 is then formed on one portion of a surface of the second polymer layer 320 and a surface of the protrusion part 321. In addition, FIG. 5D shows the cross-sectional view in which a third polymer layer 330 is formed on the surface of the second polymer layer 320 and the metal thin film layer 200. Next, FIG. 5E shows the cross-sectional view in which the first polymer layer 310, the second polymer layer 320, the metal thin film layer 200 and the third polymer layer 330 are punched to form a through hole 350, and then a conductive part 410 is formed to pass through the through hole.

As shown in FIG. 5E, the neural electrode according to another embodiment of the disclosure includes: a flexible first polymer layer 310 made of a polymer material and functioning as a base; at least one photoresist part 100 formed on one portion of a surface of the first polymer layer 310 and forming a three-dimensional structure; a second polymer layer 320 formed on the rest of the surface of the first polymer layer 310 and the photoresist part 100, and including a protrusion part 321 formed by the photoresist part 100; a metal thin film layer 200 formed by patterning a metal thin film on one portion of a surface of the second polymer layer 320 and a surface of the protrusion part 321; a third polymer layer 330 formed on the surface of the second polymer layer 320 and the metal thin film layer 200 to function as a covering, and including a measurement hole 340 punched for one portion of the metal thin film layer 200 formed at an end of the protrusion part 321 to be exposed to the outside; and the conductive part 410 passing through the first polymer layer 310 and the second polymer layer 320 to be in contact with the metal thin film layer 200, and connected to an external terminal.

Here, the through hole 350 may be formed by punching not only the first polymer layer 310 and the second polymer layer 320, but also the metal thin film layer 200 and the third polymer layer 330, and the conductive part 410 may be inserted into the through hole 350, thereby allowing the conductive part 410 and the metal thin film layer 200 to be in contact with each other. As shown in FIGS. 5C and 5D, the first polymer layer 310, the second polymer layer 320, the metal thin film layer 200 and the third polymer layer 330 may each include the punched portion to form the through hole 350. Here, the punched portion of the third polymer layer 330 may have a larger diameter than the punched portions of the other layers, thereby maximizing a contact area between the metal thin film layer 200 and the conductive part 410 and maximizing efficiency of an electrical signal exchange between the metal thin film layer 200 and the external terminal.

One or more layers selected from the first polymer layer 310, the second polymer layer 320 or the third polymer layer 330 may be made of parylene. The parylene is a plastic obtained by polymerization of paraxylene, and is harmless to a human body. In case of performing parylene coating on a predetermined surface using parylene coating equipment of the prior art, the parylene may be vapor-deposited and polymer coated on a coating object in a micrometer (μm)

thickness unit. The parylene coating equipment belongs to the prior art, and the description thus omits details of using the same.

This embodiment of the disclosure describes that one or more layers selected from the first polymer layer 310, the second polymer layer 320 or the third polymer layer 330 are formed of the parylene. However, the layers are not limited thereto, and may use any material harmless to the human body and capable of forming a coating layer having a thickness of micrometer (μm) or nanometer (nm) unit.

The photoresist part 100 may be made of photoresist which is a polymer material whose resistance to a chemical is changed by being exposed to light. The photoresist part 100 may be formed by patterning the photoresist on the first polymer layer 310 to pattern the three-dimensional structure of the photoresist, and reflowing the three-dimensional structure of the photoresist using a photoresist reflow device. The photoresist reflow device belongs to the prior art, and the description thus omits details of using the same.

One or more layers selected from the first polymer layer 310, the second polymer layer 320 or the third polymer layer 330 may be formed by vapor deposition. In detail, one or more layers selected from the first polymer layer 310, the second polymer layer 320 or the third polymer layer 330 may be formed by chemical vapor deposition. In addition, as described above, in case that each layer is made of the parylene, each layer may be formed by being chemically vapor-deposited using the parylene coating equipment.

The metal thin film layer 200 may be made of gold (Au) or platinum (Pt). The metal thin film layer 200 may be vapor-deposited on the one portion of the surface of the second polymer layer 320 and the surface of the protrusion part 321, and may be vapor-deposited by a sputtering process or a chemical vapor deposition (CVD) process.

The metal thin film layer 200 may include a measuring thin film 201 formed at the end of the protrusion part 321 and along a body surface of the protrusion part 321, and a bonding thin film 203 connected to the measuring thin film 201 and formed on one portion of the surface of the second polymer layer 320, adjacent to the protrusion part 321, and including the punched portion formed to be the through hole 350. One portion of the measuring thin film 201, exposed through the measurement hole 340, may be in contact with an object.

The measuring thin film 201 may be exposed to the outside through the measurement hole 340 and may come into contact with the object. In addition, in case that the plurality of protrusion parts 321 are formed by the plurality of photoresist parts 100, each of the plurality of measuring thin films 201 may be formed on the end and body surface of the protrusion part 321, and the plurality of bonding thin films 203 may each be connected to the plurality of measuring thin films 201. In addition, the bonding thin film 203 may come into contact with the conductive part 410 inserted into the through hole 350, and the conductive part 410 may be connected to the external terminal. An electrical signal may be exchanged between the external terminal and the measuring thin film 201 through the bonding thin film 203 and the conductive part 410.

The first polymer layer 310 may be formed on the wafer 510. Here, the sacrificial layer 520 may be formed between the first polymer layer 310 and the wafer 510. The sacrificial layer 520 may be formed between the first polymer layer 310 and the wafer 510, and may be selectively removed to perform a function of allowing the wafer 510 to be separated from the first polymer layer 310. The sacrificial layer 520 may use a material such as polyvinyl alcohol (PVA), polym-ethyl methacrylate (PMMA) or polystyrene (PS), which is selectively dissolved only in an organic solvent such as water, acetone or toluene.

The conductive part 410 may be made of conductive epoxy. In case that the through hole 350 is formed as described above, the conductive epoxy in a dissolved state may be inserted into the through hole 350 and then cured to form the conductive part 410. This embodiment of the disclosure describes that the conductive part 410 is made of the conductive epoxy. However, the conductive part 410 is not necessarily limited thereto, and may use a polymer material having conductivity as its material.

Hereinafter, the description describes a manufacturing method of the neural electrode according to another embodiment of the disclosure.

First, FIG. 5A shows a first step of preparing the wafer 510, vapor-depositing the sacrificial layer 520 on a surface of the wafer 510, and then vapor-depositing the first polymer layer 310 on a surface of the sacrificial layer 520 Next, FIG. 5B shows a second step of forming the three-dimensional structure by patterning and reflowing the photoresist part 100 on one portion of the surface of the first polymer layer 310.

In addition, FIG. 5C shows a third step of vapor-depositing the second polymer layer 320 on the rest of the surface of the first polymer layer 310 and the photoresist part 100, and then, a fourth step of vapor-depositing the metal thin film layer 200 including the punched portion by vapor-depositing and patterning the metal thin film on one portion of the surface of the second polymer layer 320 and the surface of the protrusion part 321. Here, the punched portion of the metal thin film layer 200 for forming the through hole 350 may be formed in the bonding thin film 203 by patterning the metal thin film.

In addition, FIG. 5D shows a fifth step of vapor-depositing the third polymer layer 330 on the surface of the second polymer layer 320 and the metal thin film layer 200, and etching one portion of the third polymer layer 330 to form the measurement hole 340. As described above, the measurement hole 340 may be formed by etching the one portion of the third polymer layer 330 and punching the same. The one portion of the third polymer layer 330 may be etched by using dry etching capable of fine patterning. However, the etching method is not limited thereto, and wet etching may be used.

Subsequently, FIG. 5D shows a sixth step of forming the through hole 350 by punching the first polymer layer 310, the second polymer layer 320 and the third polymer layer 330, based on the punched portion of the metal thin film layer 200. Here, the first polymer layer 310, the second polymer layer 320 and the third polymer layer 330 may be punched by an etching process. As described above, the punched portion of the third polymer layer 330 may have a larger diameter than the punched portions of the other layers.

Next, FIG. 5E shows a seventh step of separating and removing the wafer 510 and the sacrificial layer 520, and forming the conductive part 410 placed along the through hole 350 and in contact with the metal thin film layer 200. Here, the sacrificial layer 520 may be removed by being dissolved in the organic solvent. In addition, the conductive part 410 may pass through the one portion of the surface of the second polymer layer 320, and the metal thin film layer 200, the first polymer layer 310 and the third polymer layer 330, which are formed on the one portion of the surface of the second polymer layer 320, and may be in contact with the metal thin film layer 200. In addition, the conductive part 410 may be connected to the external terminal. Accordingly, the electrical signal may be exchanged between the external terminal and the measuring thin film 201 through the conductive part 410 and the bonding thin film 203.

Figure 6:
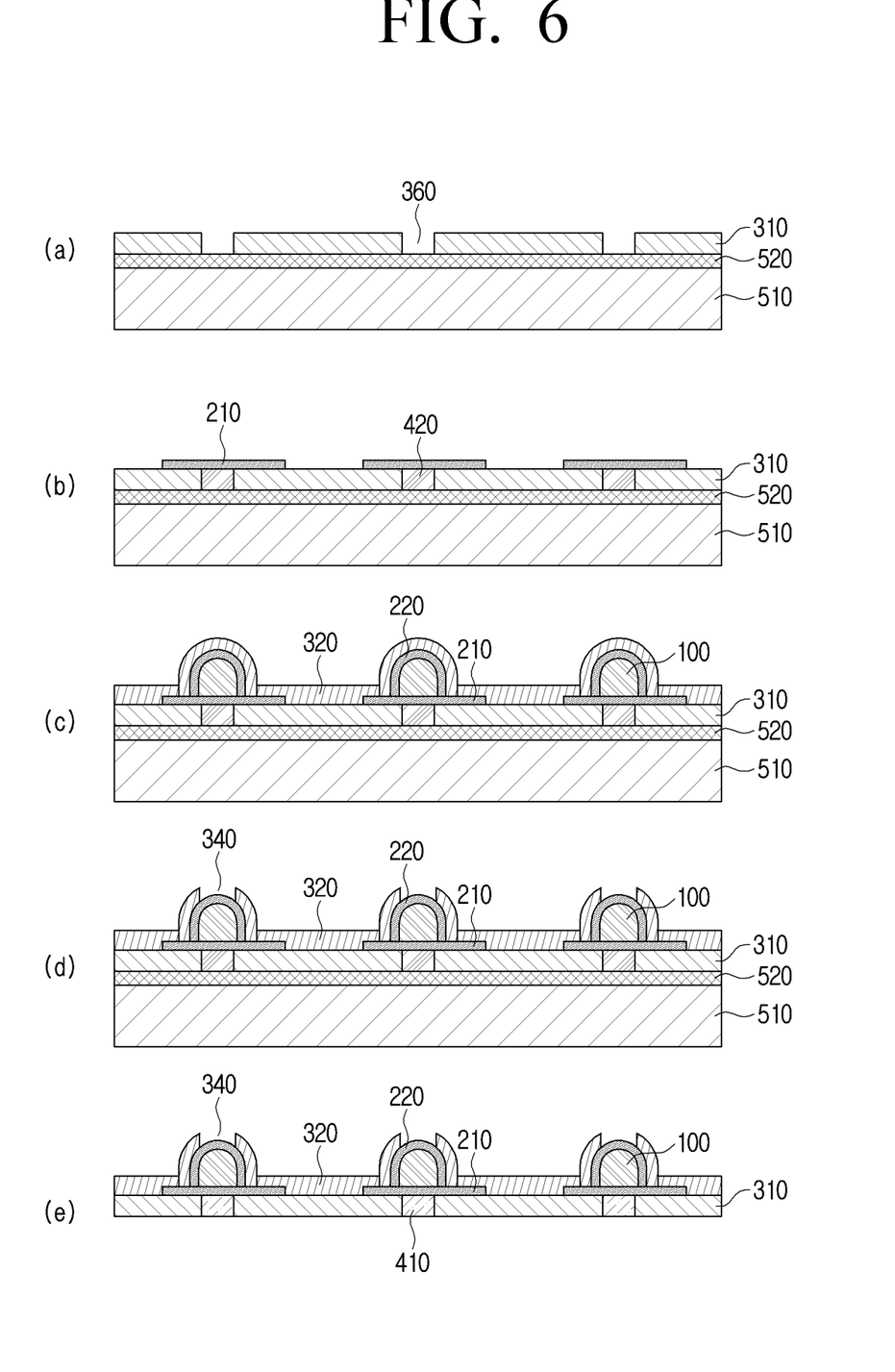
FIG. 6 shows cross-sectional views showing a manufacturing process of a neural electrode according to yet another embodiment of the disclosure.

Hereinafter, the description describes a neural electrode according to yet another embodiment of the disclosure. FIG. 6 shows cross-sectional views showing a manufacturing process of a neural electrode according to yet another embodiment of the disclosure. Here, FIG. 6A shows the cross-sectional view in which the wafer 510, the sacrificial layer 520 and the first polymer layer 310 are sequentially stacked together, and a connection hole 360 is then formed; and FIG. 6B shows the cross-sectional view in which a temporary insert 420 is inserted into the connection hole 360 and a first metal thin film layer 210 is formed on the connection hole 360 and one portion of the surface of the first polymer layer 310, adjacent to the connection hole 360. In addition, FIG. 6C shows the cross-sectional view in which the photoresist part 100 is formed on the surface of the first metal thin film layer 210, and a second metal thin film layer 220 is formed thereon. In addition, FIG. 6D shows the cross-sectional view in which the second polymer layer 320 is formed, and the measurement hole 340 is then formed by etching one portion of the second polymer layer 320. Next, FIG. 6E shows the cross-sectional view in which a conductive part 410 is formed in the connection hole 360 from which the temporary insert 420 is removed.

As shown in FIG. 6E, the neural electrode according to yet another embodiment of the disclosure includes: a flexible first polymer layer 310 made of a polymer material, functioning as a base, and including at least one punched connection hole 360; a first metal thin film layer 210 formed by patterning a metal thin film on the connection hole 360 and one portion of a surface of the first polymer layer 310, adjacent to the connection hole 360; a photoresist part 100 formed on a surface of the first metal thin film layer 210 and forming a three-dimensional structure; a second metal thin film layer 220 formed by a metal thin film on the photoresist part 100 and connected to the first metal thin film layer 210; a second polymer layer 320 formed on the first metal thin film layer 210, the second metal thin film layer 220 and the rest of the surface of the first polymer layer 310 to function as a covering, and including a measurement hole 340 punched for one portion of the second metal thin film layer 220 placed at an end of the photoresist part 100 to be exposed to the outside; and the conductive part 410 inserted into the connection hole 360 to be in contact with the first metal thin film layer 210, and connected to an external terminal.

The first polymer layer 310 or the second polymer layer 320 may be made of parylene. The parylene is a plastic obtained by polymerization of paraxylene, and is harmless to a human body. In case of performing parylene coating on a predetermined surface using parylene coating equipment of the prior art, the parylene may be vapor-deposited and polymer coated on a coating object in a micrometer (μm) thickness unit. The parylene coating equipment belongs to the prior art, and the description thus omits details of using the same.

This embodiment of the disclosure describes that one or more layers selected from the first polymer layer 310, the second polymer layer 320 or the third polymer layer 330 are formed of the parylene. However, the layers are not limited thereto, and may use any material harmless to the human body and capable of forming a coating layer having a thickness of micrometer (μm) or nanometer (nm) unit.

The photoresist part 100 may be made of photoresist which is a polymer material whose resistance to a chemical is changed by being exposed to light. The photoresist part 100 may be formed by patterning the photoresist on the first polymer layer 310 to pattern the three-dimensional structure of the photoresist, and reflowing the three-dimensional structure of the photoresist using a photoresist reflow device. The photoresist reflow device belongs to the prior art, and the description thus omits details of using the same.

The first polymer layer 310 or the second polymer layer 320 may be formed by vapor deposition. In detail, the first polymer layer 310 or the second polymer layer 320 may be formed by chemical vapor deposition. In addition, as described above, in case that each layer is made of the parylene, each layer may be formed by being chemically vapor-deposited using the parylene coating equipment.

The first metal thin film layer 210 and the second metal thin film layer 220 may each be made of gold (Au) or platinum (Pt). In addition, the first metal thin film layer 210 and the second metal thin film layer 220 may be vapor-deposited by a sputtering process or a chemical vapor deposition (CVD) process.

As shown in FIG. 6B, one portion of the first metal thin film layer 210 may be formed while sealing the connection hole 360, and the other portions of the first metal thin film layer 210 may each be formed on the one portion of the surface of the first polymer layer 310, adjacent to the connection hole 360. In addition, the second metal thin film layer 220 may be formed along the end and body surface of the photoresist part 100 forming a protruding three-dimensional structure, and the second metal thin film layer 220 formed in this way may be connected to the first metal thin film layer 210. In addition, the one portion of the second metal thin film layer 220, exposed through the measurement hole 340, may be in contact with an object.

The second metal thin film layer 220 may be exposed to the outside through the measurement hole 340 and may come into contact with the object. In addition, in case that the plurality of photoresist parts 100 are formed, each of the plurality of second metal thin film layers 220 may be formed on the end and body surface of the photoresist part 100, and the plurality of first metal thin film layers 210 may each be connected to the plurality of second metal thin film layers 220. In addition, the first metal thin film layer 210 may come into contact with the conductive part 410 inserted into the connection hole 360, and the conductive part 410 may be connected to the external terminal. An electrical signal may be exchanged between the external terminal and second metal thin film layer 220 through the first metal thin film layer 210 and the conductive part 410.

The first polymer layer 310 may be formed on the wafer 510. Here, the sacrificial layer 520 may be formed between the first polymer layer 310 and the wafer 510. The sacrificial layer 520 may be formed between the first polymer layer 310 and the wafer 510, and may be selectively removed to perform a function of allowing the wafer 510 to be separated from the first polymer layer 310. The sacrificial layer 520 may use a material such as polyvinyl alcohol (PVA), polymethyl methacrylate (PMMA) or polystyrene (PS), which is selectively dissolved only in an organic solvent such as water, acetone or toluene.

The conductive part 410 may be made of conductive epoxy. After the temporary insert 420 inserted into the connection hole 360 is removed, the conductive epoxy may be inserted into the connection hole 360 and cured to form the conductive part 410. This embodiment of the disclosure describes that the conductive part 410 is made of the conductive epoxy. However, the conductive part 410 is not necessarily limited thereto, and may use a polymer material having conductivity as its material.

Hereinafter, the description describes a manufacturing method of the neural electrode according to yet another embodiment of the disclosure.

First, FIG. 6A shows a first step of preparing the wafer 510, vapor-depositing the sacrificial layer 520 on a surface of the wafer 510, then patterning and vapor-depositing the first polymer layer 310 on a surface of the sacrificial layer 520, and forming the connection hole 360 in the first polymer layer 310. Here, the connection hole 360 may be formed by patterning the punched portion in case of forming the first polymer layer 310.

In addition, FIG. 6B shows a second step of inserting the temporary insert 420 into the connection hole 360 to fill the same, and then forming the first metal thin film layer 210 by patterning the metal thin film on the connection hole 360 and the one portion of the surface of the first polymer layer 310, adjacent to the connection hole 360. Here, the temporary insert 420 may be made of photoresist.

Next, FIG. 6C shows a third step of patterning and reflowing the photoresist part 100 by forming a three-dimensional structure of the photoresist on the surface of the first metal thin film layer 210, and a fourth step of forming the second metal thin film layer 220 by patterning the metal thin film on the photoresist part 100, and connecting the first metal thin film layer 210 and the second metal thin film layer 220 to each other.

Subsequently, FIG. 6D shows a fifth step of vapor-depositing the second polymer layer 320 on the first metal thin film layer 210, the second metal thin film layer 220 and the rest of the surface of the first polymer layer 310, and etching the one portion of the second polymer layer 320 to form the measurement hole 340. Here, the one portion of the second polymer layer 320 to be etched may be its portion in contact with the one portion of the second metal thin film layer 220 placed at the end of the photoresist part 100. As described above, the measurement hole 340 may be formed by etching the one portion of the second polymer layer 320 and punching the same. The one portion of the second polymer layer 320 may be etched by using dry etching capable of fine patterning. However, the etching method is not limited thereto, and wet etching may be used.

Then, in a sixth step, the wafer 510 and the sacrificial layer 520 may be separated and removed. Here, the sacrificial layer 520 may be removed by being dissolved in the organic solvent.

Next, in a seventh step, the temporary insert 420 inserted into the connection hole 360 may be removed, and the conductive part 410 may then be inserted into the connection hole 360 to be in contact with the first metal thin film layer 210. The temporary insert 420 may be made of the photoresist, and the temporary insert 420 may thus be removed using a solution for dissolving the photoresist. In addition, the conductive part 410 may be connected to the external terminal. Accordingly, the electrical signal may be exchanged between the external terminal and the second metal thin film layer 220 through the conductive part 410 and the first metal thin film layer 210.

As seen above, according to each of the embodiments of the disclosure, the three-dimensional structure may be formed by the photoresist part 100, the metal thin film may be formed at the end of the three-dimensional structure, and the metal thin film formed in this way to function as the electrode may be connected to the external terminal. In addition, the metal thin film placed at the end of the three-dimensional structure may be exposed to the outside through the measurement hole 340 to be in contact with the object.

The electrode may have a three-dimensional shape based on the above configuration, and the neural electrode and the object may thus have improved adhesion therebetween. Further, the neural electrode may have any of various shapes by allowing the photoresist parts 100 to form the three-dimensional structures each having a different protrusion height.

Furthermore, it is possible to make its manufacturing method simple and its structure easily modified by sequentially stacking the polymer material and the metal together, further performing only the etching process, and omitting a separate insulation process.

According to the various embodiments as described above, it is possible to provide the flexible planar neural electrode having remarkably improved selective adhesion to the object compared to a neural electrode according to the prior art.

In detail, the planar electrode according to the prior art has a limitation in that its curved surface may have poor accessibility to a target cell. A three-dimensional electrode according to the prior art has a limitation in that the electrode is manufactured based on a hard substrate, and may thus have reduced adhesion to the object, and its manufacturing method is complicated because the electrode is manufactured by growing carbon nanotube (CNT), printed using a liquid metal, etc.

However, the neural electrode according to the disclosure basically has a shape of the planar electrode, while a part of the electrode for measuring the neural signal may have the three-dimensional shape. Therefore, the neural electrode according to the disclosure may achieve selective accessibility of the three-dimensional electrode together with the high adhesion of the planar electrode. In addition, the neural electrode according to the disclosure may be applied to any of various types of neural electrodes because its manufacturing method is simple and its structure may be easily modified if necessary. In detail, the neural electrode according to the disclosure may be applied to the neural electrode that measures or stimulates a neural signal from a nerve cell of a brain or a peripheral nerve, and may be used for an artificial retina, in particular, to replace a function of a retinal photoreceptor (i.e. photoreceptor) whose function is dead due to aging. Hereinafter, the description describes an effect of the disclosure compared to the prior art in more detail in case that the neural electrode according to the disclosure is used for the artificial retina.

An artificial retina according to the prior art adopts a structure in which the neural electrode in the form of a flat film is mounted on the retina to require a tacking for its fixation. This structure may cause tissue damage and make it difficult for the neural electrode to maintain stable adhesion to a surface of the retina. In addition, in case of the artificial retina according to the prior art, it is difficult to make a close contact between the flat two-dimensional electrode and a target cell to be stimulated, and more current may thus be needed to pass therethrough for its stimulation. Accordingly, excessive current may affect not only the target cell but also its adjacent cell, thereby causing crosstalk therebetween. As a result, it is difficult to secure a clear image.

To the contrary, the neural electrode according to the disclosure may be used not only as an epi-retinal electrode, but also as a sub-retinal electrode, which are difficult to be fixed. In addition, the neural electrode according to the disclosure may have the three-dimensional structure (braille form) for closer contact with the target cell, as described above in the various embodiments. Therefore, according to the disclosure, it is possible to insert the electrode under the retina to facilitate the closer contact between the electrode and the retina, and minimize a distance between the target cell and the electrode by using the three-dimensional convex structure. In this way, it is possible to stimulate the target cell with a lower current, thereby providing the safe artificial retina. In addition, in case that the neural electrode according to the disclosure is implemented as a three-dimensional retinal electrode formed on the flexible substrate, damage to a retinal tissue may be minimized due to the three-dimensional structure having a round shape of a semicircular structure.

The above description particularly describes the effect according to the disclosure in detail by taking the case where the neural electrode according to the disclosure is implemented in the artificial retina as an example. However, this example is taken only for explaining the effect according to an embodiment of the disclosure in detail, and the disclosure is not limited thereto. That is, the neural electrode according to the disclosure may be used for any object such as the brain, an eyeball, the peripheral nerve, etc. For example, the neural electrode according to the disclosure may be utilized as a brain interface such as an electrocorticogram (ECoG) measuring electrode, and may be used not only for the human nerve cell, but also for an animal nerve cell.

The above-described embodiments are illustratively provided, and it is apparent to those skilled in the art to which the disclosure pertains that the disclosure may be embodied in another specific form without any change in its technical idea or essential characteristics. Therefore, it is to be understood that the embodiments described hereinabove are illustrative rather than being restrictive in all respects. For example, respective components each described as a single type may also be implemented in a distributed form, and similarly, components described as being distributed from each other may also be implemented in a combined form.

It is to be understood that the scope of the disclosure is defined by the claims, and includes all modifications and alternations derived from the claims and their equivalents.

The invention claimed is:

1. A neural electrode based on a three-dimensional structure of a flexible substrate, comprising:
    a flexible first polymer layer made of a polymer material and functioning as a base;
    a three-dimensional structure of photoresist part disposed on one portion of a surface of the first polymer layer;
    a second polymer layer disposed on the rest of the surface of the first polymer layer and the three-dimensional structure, and including a protrusion part formed by the three-dimensional structure;
    a metal thin film layer formed by patterning a metal thin film on a surface of the second polymer layer and a surface of the protrusion part; and
    a third polymer layer disposed on the surface of the second polymer layer and the metal thin film layer to function as a covering, and including a measurement hole that exposes one portion of the metal thin film layer disposed on an end of the protrusion part to the outside.

2. The neural electrode based on a three-dimensional structure of a flexible substrate as claimed in claim 1, wherein the first polymer layer is formed on a wafer.

3. The neural electrode based on a three-dimensional structure of a flexible substrate as claimed in claim 1, wherein one or more layers selected from the first polymer layer, the second polymer layer or the third polymer layer are formed by vapor deposition.

4. The neural electrode based on a three-dimensional structure of a flexible substrate as claimed in claim 1, wherein one or more layers selected from the first polymer layer, the second polymer layer or the third polymer layer are made of parylene.

* * * * *